US00PP33675P2

(12) United States Plant Patent
van Sambeek

(10) Patent No.: US PP33,675 P2
(45) Date of Patent: Nov. 23, 2021

(54) ***PHLOX* PLANT NAMED 'DOPHLOWOWHI'**

(50) Latin Name: ***Phlox* x *procumbens***
Varietal Denomination: Dophlowowhi

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/140,100

(22) Filed: Jan. 3, 2021

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt
(74) *Attorney, Agent, or Firm* — C. Anne Whealy

(57) ABSTRACT

A new and distinct cultivar of *Phlox* plant named 'Dophlowowhi', characterized by its upright to outwardly spreading and mounding plant habit; vigorous growth habit; freely flowering habit; relatively large white-colored flowers; and good garden performance.

1 Drawing Sheet

Botanical designation: *Phlox* x *procumbens*.
Cultivar denomination: 'DOPHLOWOWHI'.

CROSS-REFERENCED TO CLOSELY-RELATED APPLICATIONS

Title: *Phlox* Plant Named 'Dophlowoli'
Inventor: Ellen van Sambeek
Filed: Concurrently with this application application Ser. No. 17/140,094

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Aug. 12, 2020, application number 2020/1897. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Phlox* plant, botanically known as *Phlox* x *procumbens* and hereinafter referred to by the name 'Dophlowowhi'.

The new *Phlox* plant is a product of a planned breeding program conducted by the Inventor in Aalsmeer, The Netherlands. The objective of the breeding program was to create new freely-flowering *Phlox* plants with large attractive flowers.

The new *Phlox* plant originated from a cross-pollination made by the Inventor in April, 2013 in Aalsmeer, The Netherlands, of a proprietary selection of *Phlox* x *procumbens* identified as code number SB-0042, not patented, as the female, or seed, parent with a proprietary selection of *Phlox* x *procumbens* identified as code number SB10-000002-005, not patented, as the male, or pollen, parent. The new *Phlox* plant was discovered and selected by the Inventor as a single flowering plant from within the progeny of the stated cross-pollination in a controlled environment in Aalsmeer, The Netherlands in April, 2014.

Asexual reproduction of the new *Phlox* plant by vegetative cuttings in a controlled environment in Aalsmeer, The Netherlands since June, 2014 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dophlowowhi'. These characteristics in combination distinguish 'Dophlowowhi' as a new and distinct *Phlox* plant:

1. Upright to outwardly spreading and mounding plant habit.
2. Vigorous growth habit.
3. Freely flowering habit.
4. Relatively large white-colored flowers.
5. Good garden performance.

Plants of the new *Phlox* differ primarily from plants of the female parent selection in plant habit as plants of the new *Phlox* are more compact than plants of the female parent selection. In addition, plants of the new *Phlox* have shorter peduncles than plants of the female parent selection.

Plants of the new *Phlox* differ primarily from plants of the male parent selection in plant habit as plants of the new *Phlox* are more upright than and not as creeping as plants of the male parent selection.

Plants of the new *Phlox* can be compared to *Phlox* x *procumbens* 'Dophlowoli', disclosed in a U.S. Plant Patent filed concurrently, in flower color as plants of the new *Phlox* have white-colored flowers whereas plants of 'Dophlowoli' have light purple-colored flowers.

Plants of the new *Phlox* can also be compared to plants of *Phlox* x *procumbens* 'Emerald Cushion Blue', not patented. In side-by-side comparisons, plants of the new *Phlox* and 'Emerald Cushion Blue' differ in the following characteristics:

1. Plants of the new *Phlox* are more upright than and not as creeping as plants of 'Emerald Cushion Blue'.
2. Plants of the new *Phlox* have larger flowers than plants of 'Emerald Cushion Blue'.
3. Plants of the new *Phlox* and 'Emerald Cushion Blue' differ in flower color as plants of the new *Phlox* have white-colored flowers whereas plants of 'Emerald Cushion Blue' have light blue-colored flowers.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant. The photograph comprises a side perspective view of typical flowering plant of 'Dophlowowhi' grown in a container.

DETAILED BOTANICAL DESCRIPTION

The aforementioned photograph and following observations, measurements and values describe plants grown during the end of winter and early spring in 17-cm containers initially in a glass-covered greenhouse and finished in an outdoor nursery in Aalsmeer, The Netherlands and under cultural practices typical of commercial *Phlox* production. During the production of the plants, day temperatures averaged 21° C. and night temperatures averaged 15° C. Plants were pinched one time two weeks after planting rooted young plants and plants were 37 weeks old when the photograph and the description were taken. In the following description, color references are made to The Royal Horticultural Society Colour Chart, Second Edition, except where general terms of ordinary dictionary significance are used.

Botanical classification: *Phlox* x *procumbens* 'Dophlowowhi'.

Parentage:

*Female, or seed, parent*.—Proprietary selection of *Phlox* x *procumbens* identified as code number SB-0042, not patented.

*Male, or pollen, parent*.—Proprietary selection of *Phlox* x *procumbens* identified as code number SB10-000002-005, not patented.

Propagation:

*Type*.—By vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Medium in thickness, fibrous; typically white to light yellow in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright to outwardly spreading and mounding plant habit; vigorous growth habit and relatively slow growth rate.

*Plant height*.—About 11 cm.

*Plant width* (*spread*).—About 19 cm.

*Lateral branches*.—Branching habit: Freely branching habit with numerous primary and secondary lateral branches developing per plant. Length: About 15 cm. Internode length: About 1.5 cm. Strength: Strong. Aspect: About 20° to 80° from vertical. Texture and luster: Pubescent; semi-glossy. Color: Close to 138A; with development, close to 138A tinged with close to 178A.

Leaf description:

*Arrangement*.—Opposite, decussate; simple; sessile.

*Length*.—About 2 cm.

*Width*.—About 7 mm.

*Shape*.—Lanceolate.

*Apex*.—Acuminate.

*Base*.—Cuneate.

*Margin*.—Entire, slightly ciliate.

*Texture and luster, upper surface*.—Slightly pubescent; semi-glossy.

*Texture and luster, lower surface*.—Slightly pubescent; glossy.

*Venation pattern*.—Hyphodromous.

*Color*.—Developing leaves, upper surface: Close to 143C. Developing leaves, lower surface: Close to 141D. Fully expanded leaves, upper surface: Close to 147A; venation, close to 139A. Fully expanded leaves, lower surface: Close to 147B; venation, close to 139A.

Flower description:

*Flower type and flowering habit*.—Single rotate and salverform flowers arranged in terminal and lateral panicles; flowers face mostly upright to outwardly depending on position on inflorescence; freely flowering habit with about three open flowers per inflorescence and about 333 flowers developing per plant during the flowering season.

*Fragrance*.—Not detected.

*Natural flowering season*.—Plants begin flowering about 35 weeks after planting; plants flower in April and May in the garden in The Netherlands; flowers persistent.

*Flower buds*.—Height: About 1.9 cm. Diameter: About 4 mm. Shape: Elliptical. Texture and luster: Smooth, glabrous; matte. Color: Close to 155A.

*Inflorescence height*.—About 8 cm.

*Inflorescence diameter*.—About 7 cm.

*Flower diameter*.—About 2.2 cm by 2.2 cm.

*Flower depth*.—About 1.5 cm.

*Flower throat diameter*.—About 2 mm.

*Flower tube length*.—About 6 mm.

*Flower diameter, proximally*.—About 2 mm.

*Petals*.—Quantity per flower: Typically five in a single whorl; petals fused at the base into a narrow tube. Lobe length: About 1 cm. Lobe width: About 8 mm. Lobe shape: Obovate. Lobe apex: Rounded. Lobe margin: Entire; slightly undulate. Lobe texture and luster, upper and lower surfaces: Smooth, glabrous; matte. Throat texture and luster: Smooth, glabrous; matte. Tube texture and luster: Pubescent; matte. Color: When opening, upper and lower surfaces: Close to 155D. Fully opened, upper and lower surfaces: Close to 155D; color does not change with development. Throat: Close to 155D; venation, close to 155D. Tube: Close to 155C; venation, close to 155C.

*Sepals*.—Quantity per flower: Typically five in a single whorl, fused towards the base; calyx, tubular in shape. Length: About 7 mm. Width: About 1 mm. Shape: Narrowly deltoid, subulate. Apex: Acuminate. Margin: Entire. Texture and luster, upper and lower surfaces: Pubescent; glossy. Color: When opening and fully opened, upper surface: Close to 141A. When opening and fully opened, lower surface: Close to 137A.

*Peduncles*.—Length: About 4 cm. Diameter: About 2 mm. Strength: Moderately strong. Aspect: About 40° from lateral branch axis. Texture and luster: Pubescent; semi-glossy. Color: Close to 138A tinged with close to 178A.

*Pedicels*.—Length: About 1.3 cm. Diameter: About 1 mm. Strength: Moderately strong. Aspect: About 5° to 35° from peduncle axis. Texture and luster: Pubescent; semi-glossy. Color: Close to 147A.

*Reproductive organs*.—Stamens: Quantity per flower: Typically five. Filament length: About 6 mm. Filament color: Close to 155C. Anther length: About 1 mm. Anther shape: Elliptical. Anther color: Close to 21A. Pollen amount: Abundant. Pollen color: Close to 21A. Pistils: Quantity per flower: One. Pistil length: About 7 mm. Stigma diameter: About 0.5 mm. Stigma shape: Cleft, three-parted. Stigma color: Close to 150A. Style length: About 5 mm. Style color: Close to 149A. Ovary color: Close to 140A.

*Seeds and fruits*.—To date, seed and fruit development have not been observed on plants of the new *Phlox*.

Garden performance: Plants of the new *Phlox* have been observed to have good garden performance and to tolerate rain, wind, temperatures ranging from −35° C. to 35° C. and to be suitable for USDA Hardiness Zone 3.

Pathogen & pest resistance: To date, plants of the new *Phlox* have not been observed to be resistant to pathogens and pests common to *Phlox* plants.

It is claimed:

1. A new and distinct *Phlox* plant named 'Dophlowowhi' as illustrated and described.

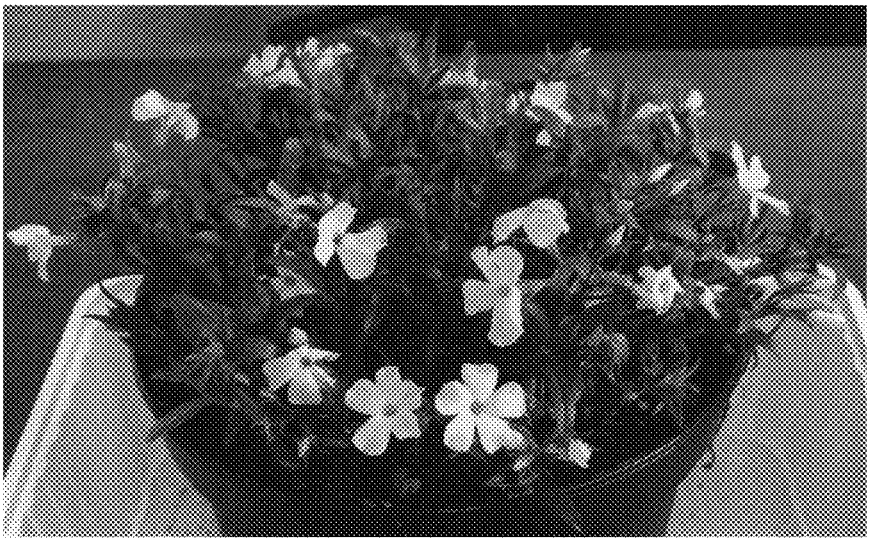

* * * * *